United States Patent
Bru Roig et al.

(10) Patent No.: US 10,053,409 B2
(45) Date of Patent: Aug. 21, 2018

(54) PROCESS FOR PREPARING 3-METHYLCYCLOPENTADECANE-1,5-DIONE

(71) Applicant: BASF SE, Ludwigshafen (DE)

(72) Inventors: Miriam Bru Roig, Heidelberg (DE); Stefan Rüdenauer, Weinheim (DE)

(73) Assignee: BASF SE (DE)

( * ) Notice: Subject to any disclaimer, the term of this patent is extended or adjusted under 35 U.S.C. 154(b) by 0 days.

(21) Appl. No.: 15/578,959

(22) PCT Filed: Jun. 2, 2016

(86) PCT No.: PCT/EP2016/062434
§ 371 (c)(1),
(2) Date: Dec. 1, 2017

(87) PCT Pub. No.: WO2016/193330
PCT Pub. Date: Dec. 8, 2016

(65) Prior Publication Data
US 2018/0179136 A1    Jun. 28, 2018

(30) Foreign Application Priority Data

Jun. 3, 2015  (EP) .................................... 15170490

(51) Int. Cl.
| | | |
|---|---|---|
| C07C 45/28 | (2006.01) | |
| C07C 45/57 | (2006.01) | |
| C07C 45/27 | (2006.01) | |
| C01B 15/01 | (2006.01) | |
| C07C 49/385 | (2006.01) | |

(52) U.S. Cl.
CPC .............. C07C 45/27 (2013.01); C01B 15/01 (2013.01); C07C 49/385 (2013.01); *C07C 2601/18* (2017.05)

(58) Field of Classification Search
CPC .................................. C07C 45/28; C07C 45/57
See application file for complete search history.

(56) References Cited

FOREIGN PATENT DOCUMENTS

| | | |
|---|---|---|
| CH | 513971 A | 10/1971 |
| CH | 519454 A | 2/1972 |
| CN | 102786398 A | 11/2012 |
| DE | 2916418 A1 | 11/1980 |
| GB | 1205047 A | 9/1970 |
| GB | 1211697 A | 11/1970 |
| GB | 1232010 A | 5/1971 |
| WO | WO-2016184948 A1 | 11/2016 |

OTHER PUBLICATIONS

Chapuis, C., et al., "Synthesis of Deuterium-Labled Perfume Ingredients as Internal Standards for Their GC/MS Quantification", Helvetica Chimica Acta, vol. 92, No. 9 (2009), pp. 1782-1799.
Database WPI, Thompson Scientific, XP-002750698, Database for Chinese Patent No. CN102786398A (Xinxiang Medical University), (2012).
International Search Report for PCT/EP2016/062434 dated Jul. 25, 2016.
Written Opinion of the International Searching Authority for PCT/EP2016/062434 dated Jul. 25, 2016.
International Preliminary Report on Patentability with Written Opinion for International Application No. PCT/EP2016/062434, dated Dec. 5, 2017.

*Primary Examiner* — Sikarl A Witherspoon
(74) *Attorney, Agent, or Firm* — Brinker Biddle & Reath LLP

(57) ABSTRACT

The present invention relates to a process for producing 3-methylcyclopentadecane-1,5-dione of formula (I), which comprises the oxidation of 14-methyl-bicyclo[10.3.0]pentadecen[1 (12)] of formula (II) with an oxidizing agent, where the oxidation is performed by using a mixture of formic acid with $H_2O_2$ as sole oxidizing agent in the presence of water and where the amount of $H_2O_2$ is at least 1.1 mol $H_2O_2$ per mol of the compound of formula (II).

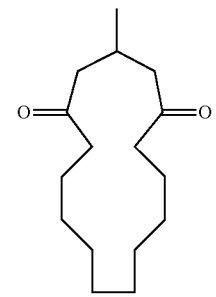

(I)

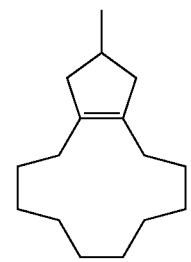

(II)

16 Claims, No Drawings

PROCESS FOR PREPARING 3-METHYLCYCLOPENTADECANE-1,5-DIONE

CROSS-REFERENCE TO RELATED APPLICATIONS

This application is a national stage application (under 35 U.S.C. § 371) of PCT/EP2016/062434, filed Jun. 2, 2016, which claims benefit of European Application No. 15170490.5, filed Jun. 3, 2015, both of which are incorporated herein by reference in their entirety.

The present invention relates to a process for preparing 3-methylcyclopentadecane-1,5-dione (I) by oxidation of 14-methylbicyclo[10.3.0]pentadecen[1(12)] of formula (II) with an oxidizing agent.

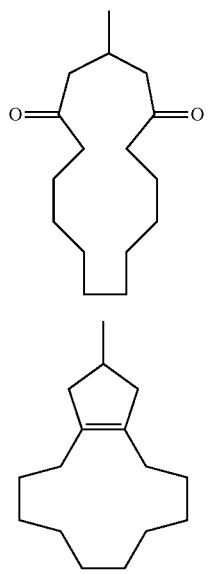

3-Methylcyclopentadecane-1,5-dione is a macrocyclic diketone of the formula (I) having interesting olfactory properties. It may also serve as precursor for other macrocyclic musk odorants, such as muscone.

CH 519454 describes the preparation of cyclopentadecane-1,5-dione by ozonolysis of bicyclo[10.3.0]pentadecen[1(12)] or photooxidation of bicyclo[10.3.0]pentadecen[1(12)] with singlet oxygen, followed by acidic rearrangement of the resulting hydroperoxides. CH 519454 also describes the reaction of bicyclo[10.3.0]pentadecen[1(12)] with potassium permanganate. Ozonolysis and photooxidation are difficult to handle on large scale, while the workup the reaction mixture obtained by oxidation with potassium permanganate is difficult and produces waste.

CH 513791 describes the preparation of cyclopentadecane-1,5-dione, comprising the oxidation of bicyclo[10.3.0]pentadecen[1(12)] with a sub-stochiometric amount of 55% aqueous $H_2O_2$ in concentrated formic acid followed by reacting the intermediate with potassium hydroxide to yield bicyclo[10.3.0]pentadecan-1,12-diol, which is then cleaved by treatment with $Pb_3O_4$ in glacial acetic acid. The process is tedious and includes the use of toxic chemicals.

Therefore, it is an object of the present invention to provide a process for efficiently producing 3-methylcyclopentadecane-1,5-dione of formula (I). The process should be easy to handle provide good yields of the compound of formula (I). Moreover, the use of toxic or expensive reagents should be avoided.

It was surprisingly found that 14-methylbicyclo[10.3.0]pentadecen[1(12)] of formula (II) can be efficiently converted into 3-methylcyclopentadecane-1,5-dione of formula (I), if the oxidation of 14-methylbicyclo[10.3.0]pentadecen[1(12)] is performed by using a mixture of formic acid with $H_2O_2$ as sole oxidizing agent in the presence of water and where the amount of $H_2O_2$ is at least 1.1 mol $H_2O_2$ per mol of 14-methylbicyclo[10.3.0]-pentadecen[1(12)]. Surprisingly, only traces of 3-methylcyclopentadecane-1,5-dione (I) are formed, when reacting 14-methylbicyclo[10.3.0]pentadecen[1(12)] (II) with sub-stoichiometric amounts of $H_2O_2$ in formic acid under the conditions described in CH513791. Moreover, the allegedly formed 3-methylbicyclo[10.3.0]pentadecan-1,12-diol could not be found.

Therefore, the present invention relates to a process for producing 3-methylcyclopentadecane-1,5-dione of formula (I), which comprises the oxidation of 14-methylbicyclo[10.3.0]pentadecen[1(12)] of formula (II) with an oxidizing agent, where the oxidation is performed by using a mixture of formic acid with $H_2O_2$ as sole oxidizing agent in the presence of water and where the amount of $H_2O_2$ is at least 1.1 mol $H_2O_2$ per mol of the compound of formula (II).

The process has several advantages over prior art. The oxidation of the compound of the formula (II) by using a mixture of $H_2O_2$ and formic acid in the presence of water by the process as described herein, directly results in the formation of the compound of the formula (I) with at least moderate yields and selectivity. In contrast to the process described in CH 513791, no subsequent reaction steps are required. In contrast to the methods described in CH 519454 the process can be easily performed on large scale, as $H_2O_2$ is much easier to handle than ozone or singlet oxygen. Moreover $H_2O_2$ and formic acid are cheap and thus expensive or toxic oxidants such as potassium permanganate or $Pb_3O_4$ are not required.

Without being bound by theory, it is believed that the peroxoformic acid, which is formed in the mixture of $H_2O_2$ and formic acid reacts with the compound of formula (II) to form primarily an epoxide, which under the reaction conditions is further attacked by hydrogen peroxide or peroxoformic acid to form an adduct which cleaves to the compound of formula (I).

It was found that a minimum amount of at least 1.1 mol, frequently 1.2 mol, in particular at least 1.4 mol, especially at least 1.5 mol $H_2O_2$ per mol of the compound of formula (II) is required to achieve a good conversion of the compound of the formula (II). The upper amount of $H_2O_2$ is less critical, however, the amount of $H_2O_2$ will usually not exceed 5.0 mol, in particular 4.0 mol and especially 3.5 mol, per mol of the compound of the formula (II). Frequently, the amount of $H_2O_2$ is from 1.2 to 5.0 mol, in particular 1.4 to 4.0 mol $H_2O_2$, especially from 1.5 to 3.3 mol $H_2O_2$ per mol of the compound of the formula (II).

The reaction can be principally performed in accordance with standard procedures of organic chemistry.

It was found beneficial, if at least a part, e.g. at least 30%, in particular at least 50% or at least 70% of the $H_2O_2$ used for the reaction or the total amount of the $H_2O_2$ used for the reaction is added to a mixture of the compound of formula (II) and formic acid. The mixture may contain water before $H_2O_2$ is added. However the water may also be introduced by the addition of $H_2O_2$, e.g. by addition of aqueous $H_2O_2$. In particular, the compound of formula (II) and formic acid and optionally water are charged to a reaction vessel and a part, e.g. at least 30%, in particular at least 50% or at least 70% of the $H_2O_2$ used for the reaction or the total amount of the $H_2O_2$ used for the reaction is added to the thus obtained mixture of the compound of formula (II) and formic acid, which optionally contains water.

It was found beneficial, if less than 70%, in particular at most 50%, especially at most 30% of the total amount of $H_2O_2$ used as oxidizing agent is present at the beginning of the oxidation. Consequently, at least 30%, in particular at least 50% or at least 70% of the $H_2O_2$ used for the reaction or the total amount of the $H_2O_2$ used for the reaction is added to the mixture of the compound of formula (II) and formic acid under reaction conditions.

The portion $H_2O_2$, which is added to the mixture of the compound of formula (II) and formic acid, may be added in one or more portions or continuously with constant or changing addition rates. It was found beneficial, if the $H_2O_2$ is added over a period of at least 2 h, in particular at least 3 h e.g. from 2 to 24 h especially from 3 to 18 h.

Preferably, $H_2O_2$ is used as an aqueous solution, where the concentration of $H_2O_2$ in the aqueous $H_2O_2$ is in particular from 20 to 50% by weight and more particularly from 25 to 40% by weight.

According to the invention, the oxidation of the compound of formula (II) to the compound of formula (I) is performed in the presence of formic acid. In particular, the weight ratio of the compound of formula (II) and the formic acid is at most 1:1, in particular at most 1:1.5 or at most 1:2, and especially in the range from 1:20 to 1:2.

According to the invention, the oxidation of the compound of formula (II) to the compound of formula (I) is performed in the presence of water. The amount of water may be added to the reaction mixture either by using aqueous $H_2O_2$ or by using aqueous formic acid or both. Of course, water may also be added separately. Preferably, the concentration of water in the reaction mixture is from 3 to 25% by weight.

The temperature, which is required to achieve the oxidation of the compound of formula (II) to the compound of formula (I) may vary. Frequently, the oxidation of the compound of formula (II) to the compound of formula (I) is performed at a temperature of −20 to 100° C., in particular from 0 to 80° C. and especially from 10 to 60° C.

The reaction pressure is of minor importance. In particular the reaction is performed in a non-pressured vessel having pressurized balance with the ambient air.

The process of the invention can be designed to take place either continuously or batchwise. The batchwise oxidation can be conducted in a reaction apparatus conventionally used for this purpose, e.g. a stirred reactor, which is optionally equipped with metering devices. The process according to the present invention may also be carried out continuously, e.g. in a tube reactor or in a cascade of at least two stirred reactors, which may be back-mixed or not.

The reaction mixture can be subjected to conventional work-up including e.g. extractive aqueous work-up, removal of volatiles and the like. Usually, any excess of peroxide will be destroyed prior to or during work-up of the reaction mixture by addition of suitable reducing agents, such as aqueous thiosulfate, sulfite, bisulfite, ascorbic acid or triphenylphosphine.

The obtained crude product may be subjected to conventional purification measures, including distillation or chromatography or combined measures. Suitable distillation devices for the purification of the compounds of formula (I) include, for example, distillation columns, such as tray columns optionally equipped with bubble cap trays, sieve plates, sieve trays, packages or filler materials, or spinning band columns, such as thin film evaporators, falling film evaporators, forced circulation evaporators, Sambay evaporators, etc. and combinations thereof.

14-Methylbicyclo[10.3.0]pentadecen[1(12)], which is used as a starting material is known e.g. from DE 2916418 or commercially available or it can be prepared by analogy to the methods described in DE 2916418.

EXAMPLES

I) Gas Chromatographic Analysis

GC-System and Separation Method:
GC-system: Agilent 7890 Series A;
GC-Column: DB-WAX (30 m (Length), 0.32 mm (ID), 0.25 μm (Film));
Injector at 230° C., detector at 280° C. and flow 1.5 mL.
Temperature program: 80° C. to 250° C. in 3° C./min, 250° C. for 15 min.

II) Production Examples

Comparative Example 1 (According to CH 513791)

2.5 g (0.01 mol) of 14-methylbicyclo[10.3.0]pentadecen [1(12)] were dissolved at 22° C. in 30 mL of concentrated formic acid (90%). The mixture was heated to 40° C. At this temperature 0.55 g of 50% (w/w) aqueous $H_2O_2$ (8 mmol, 0.8 eq.) were added drop wise. After having completed the addition, the reaction mixture was stirred at 40° C. for 6 h. Then, the reaction mixture was cooled down to 22° C. and left standing overnight. Then 15 mL of a 10% (w/w) aqueous $Na_2SO_3$ solution were slowly added and the reaction mixture was stirred at 22° C. for 1 h. Then, the reaction mixture was evaporated at reduced pressured and 15 mL of ethanol were added to the residue followed by 40 mL of a 10% (w/w) aqueous KOH solution. The mixture was stirred for 4 h at 22° C. and the product was extracted with ethyl acetate. The organic phase was washed with water and the solvent was evaporated in the rotavapor to obtain 2 g of a crude product which contained 82% (GC area) of 14-methylbicyclo [10.3.0]pentadecen[1(12)] and a 3% (GC area %) of 3-methylcyclopentadecane-1,5-dione.

Comparative Example 2 (According to CH 513791 but with 35% $H_2O_2$)

2.5 g (0.01 mol) of 14-methylbicyclo[10.3.0]pentadecen [1(12)] were dissolved at 22° C. in 30 mL of concentrated formic acid (90%). The mixture was heated to 40° C. At this temperature 0.8 g of 35% (w/w) aqueous $H_2O_2$ (0.8 eq.) were added dropwise. After having completed the addition, the reaction mixture was stirred at 40° C. for 6 h. Then, the reaction mixture was cooled down to 22° C. and left standing overnight. Then 15 mL of a 10% (w/w) aqueous $Na_2SO_3$ solution were slowly added and the reaction mixture was stirred at 22° C. for 1 h. Then, the reaction mixture was evaporated at reduced pressured and 15 mL of ethanol were added to the residue followed by 40 mL of a 10% (w/w) aqueous KOH solution. The mixture was stirred for 4 h at 22° C. and the product was extracted with ethyl acetate. The organic phase was washed with water and the solvent was evaporated in the rotavapor to obtain 2 g of a crude product which contained 76% (GC area) of 14-methylbicyclo

[10.3.0]pentadecen[1(12)] and a 8% (GC area %) of 3-methylcyclopentadecane-1,5-dione.

Example 1 (3.2 eq. of $H_2O_2$)

2.5 g (0.01 mol) of 14-methylbicyclo[10.3.0]pentadecen [1(12)] were dissolved at 22° C. in 30 mL of concentrated formic acid (90%). The mixture was heated to 40° C. At this temperature 3.1 g of 35% (w/w) aqueous $H_2O_2$ (32 mmol, 3.2 eq.) were added dropwise. After having completed the addition, the reaction mixture was stirred at 40° C. for 3 h. Then, the reaction mixture was cooled down to 22° C. and 30 mL of a 10% (w/w) aqueous $Na_2SO_3$ solution were slowly added. Then, the reaction mixture was extracted with dichloromethane. The organic phase was collected and after a negative test for peroxide the organic solvents were evaporated in a rotavap. The obtained oil was re-dissolved in ethyl acetate and the solution was washed with a 10% (w/w) aqueous KOH solution and with water. The organic phase was dried with $Na_2SO_4$ and the solvent was evaporated under reduced pressure to obtain 2.1 g of a crude product which contained 43% (GC area %) of 3-methylcyclopentadecane-1,5-dione, representing a yield of 36%, based on 14-methylbicyclo[10.3.0]pentadecen[1(12)].

Example 2 (3.2 eq. of $H_2O_2$, Large Scale)

70 g (0.317 mol) of 14-methylbicyclo[10.3.0]pentadecen [1(12)] were dissolved at 22° C. in 300 mL of concentrated formic acid (90%). The mixture was heated to 40° C. At this temperature 115 mL of 30% (w/w) aqueous $H_2O_2$ (1.014 mmol, 3.2 eq.) were added drop wise. After having completed the addition, the reaction mixture was stirred at 40° C. for 3 h. Then, the reaction mixture was cooled down to 22° C. and 300 mL of a 20% (w/w) aqueous $Na_2SO_3$ solution were slowly added. Then, the reaction mixture was extracted with dichloromethane. The organic phase was collected and after a negative test for peroxide the organic solvents were evaporated in a rotavap. The obtained oil was re-dissolved in ethyl acetate and the solution was washed with a 10% (w/w) aqueous KOH solution and with water. The organic phase was dried with $Na_2SO_4$ and the solvent was evaporated under reduced pressure to obtain 80.1 g of a crude product which contained 23% (GC weight %) of 3-methylcyclopentadecane-1,5-dione, representing a yield of 25%, based on 14-methylbicyclo[10.3.0]pentadecen[1(12)].

Example 3 ($H_2O_2$ Dosing)

5 g (0.02 mol) of 14-methylbicyclo[10.3.0]pentadecen[1 (12)] were dissolved at 22° C. in 30 mL of concentrated formic acid (90%). The mixture was heated to 40° C. At this temperature 1.8 g of 30% (w/w) aqueous $H_2O_2$ (0.016 mmol, 0.8 eq.) were added drop wise. After having completed the addition, the reaction mixture was stirred at 40° C. for 3 h. Then, a sample was taken and—after work-up as described for example 1—the sample was analyzed by GC. Then, further 1.8 g of 30% (w/w) aqueous $H_2O_2$ were added and the mixture was stirred for 3 additional hours at 40° C. This procedure was repeated two times. After each reaction period of 3 h, samples were taken and analyzed by GC after work-up. Then the reaction mixture was cooled down to 22° C. and 30 mL of a 10% (w/w) aqueous $Na_2SO_3$ solution were slowly added. Then, the reaction mixture was extracted with ethyl acetate. The organic phase was washed with saturated aqueous $NaHCO_3$ and water. The organic extracts were collected, dried with $Na_2SO_4$ and the solvent was evaporated under reduced pressure. By stopping the reaction after the addition of 1.6 eq of $H_2O_2$ (2×0.8 eq) a maximum selectivity of 77% for 3-methylcyclopentadecane-1,5-dione could be obtained.

| Sample | Conversion(%)* | Diketone (%) | Selectivity(%)** |
|---|---|---|---|
| 3 h (0.8 eq $H_2O_2$) | 14% | 9.5% | 70% |
| 6 h (2 × 0.8 eq $H_2O_2$) | 65% | 50% | 77% |
| 9 h (3 × 0.8 eq $H_2O_2$) | 82% | 54% | 66% |
| 12 h (4 × 0.8 eq $H_2O_2$) | 100% | 55% | 55% |

*Based on 14-methylbicyclo[10.3.0]pentadecen[1(12)] GC area %.
**Based on 3-methylcyclopentadecane-1,5-dione GC area %.

The invention claimed is:

1. A process for preparing 3-methylcyclopentadecane-1,5-dione, which comprises oxidizing 14-methylbicyclo[10.3.0]pentadecen[1(12)] with an oxidizing agent, where the oxidation is performed by using a mixture of formic acid with $H_2O_2$ as sole oxidizing agent in the presence of water and where the amount of $H_2O_2$ is at least 1.1 mol $H_2O_2$ per mol of 14-methylbicyclo[10.3.0]pentadecen[1(12)].

2. The process of claim 1, wherein the amount of $H_2O_2$ is from 1.4 to 4.0 mol $H_2O_2$ per mol of 14-methylbicyclo[10.3.0]pentadecen[1(12)].

3. The process of claim 1, wherein the amount of $H_2O_2$ is from 1.5 to 3.5 mol $H_2O_2$ per mol of 14-methylbicyclo[10.3.0]pentadecen[1(12)].

4. The process of claim 1, wherein $H_2O_2$ is added to the mixture of 14-methylbicyclo[10.3.0]pentadecen[1(12)] and formic acid.

5. The process of claim 3, wherein the total amount of added $H_2O_2$ is added over a period of at least 2 h.

6. The process of claim 3, wherein the total amount of added $H_2O_2$ is added over a period of from 2 to 24 h.

7. The process of claim 3, wherein less than 70% of the total amount of $H_2O_2$ used in the process is present at the beginning of the oxidation.

8. The process of claim 3, wherein less than 70% and at most 50% of the total amount of $H_2O_2$ used in the process is present at the beginning of the oxidation.

9. The process of claim 5, wherein at least 50% of the total amount of $H_2O_2$ are added to the reaction mixture while the oxidation reaction takes place.

10. The process of claim 1, wherein the oxidation of the compound of 14-methylbicyclo[10.3.0]pentadecen[1(12)] is performed at a temperature of −20 to 100° C.

11. The process of claim 1, wherein the oxidation of the compound of 14-methylbicyclo[10.3.0]pentadecen[1(12)] is performed at a temperature of from 0 to 80° C.

12. The process of claim 1, wherein the oxidation of the compound of 14-methylbicyclo[10.3.0]pentadecen[1(12)] is performed at a temperature of from 10 to 60° C.

13. The process of claim 1, wherein the concentration of water in the reaction mixture is from 3 to 25% by weight.

14. The process of claim 1, wherein $H_2O_2$ is used as an aqueous solution.

15. The process of claim 14, wherein the concentration of $H_2O_2$ in the aqueous $H_2O_2$ is from 25 to 50% by weight.

16. The process of claim 1, where the weight ratio of 14-methylbicyclo[10.3.0]pentadecen[1(12)] and the formic acid is in the range from 1:20 to 1:2.

* * * * *